| United States Patent [19] | [11] | Patent Number: | 4,894,472 |
|---|---|---|---|
| Seng et al. | [45] | Date of Patent: | Jan. 16, 1990 |

[54] DICYANOETHYLARYL DERIVATIVES AND PROCESS FOR THEIR PREPARATION

[75] Inventors: Florin Seng, Gladbach; Klaus Wehling, Wuppertal, both of Fed. Rep. of Germany

[73] Assignee: Miles Inc., Elkhart, Ind.

[21] Appl. No.: 170,754

[22] Filed: Mar. 21, 1988

[51] Int. Cl.$^4$ .................. C07C 121/66; C12Q 1/28
[52] U.S. Cl. ............................. 558/405; 435/28; 544/163; 544/393; 544/395; 546/230; 548/577; 549/362; 549/436; 549/437; 549/439; 549/440; 558/404; 558/406; 558/409
[58] Field of Search .............. 558/409, 405, 404, 406; 435/28

[56] References Cited

U.S. PATENT DOCUMENTS

| 2,733,258 | 1/1956 | Hein | 558/409 X |
|---|---|---|---|
| 2,803,640 | 8/1957 | Heckert | 558/409 X |
| 2,806,037 | 9/1957 | Miller | 558/409 X |
| 2,940,977 | 6/1960 | Middleton | 558/409 X |
| 3,092,653 | 6/1963 | Wilkinson et al. | 558/409 |
| 3,183,245 | 5/1965 | Miller et al. | 558/409 X |
| 3,376,220 | 4/1968 | Anderson et al. | 558/409 X |
| 3,679,671 | 7/1972 | Peterson | 558/409 X |

OTHER PUBLICATIONS

McKusick et al., J.A.C.S., 80, (1958), pp. 2806–2815.

*Primary Examiner*—Joseph Paul Brust
*Attorney, Agent, or Firm*—Roger N. Coe

[57] ABSTRACT

The invention relates to new dicyanoethylaryl derivatives and to processes for their preparation. The compounds according to the invention can be used as redox indicators, such as, for example, for the detection of hydrogen peroxide with the aid of peroxidases or peroxidatively active substances.

These redox indicators are futhermore suitable for the detection of peroxidases or peroxidatively active compounds, it also being possible to use other peroxides as oxidizing agents.

2 Claims, No Drawings

DICYANOETHYLARYL DERIVATIVES AND PROCESS FOR THEIR PREPARATION

The invention relates to novel dicyanoethylaryl derivatives and to processes for their preparation. The compounds according to the invention can be used as redox indicators, such as, for example, for the detection of hydrogen peroxide with the aid of peroxidases or peroxidatively active substances.

These redox indicators are furthermore suitable for the detection of peroxidases or peroxidatively active compounds, it also being possible to use other peroxides as oxidizing agents.

Hydrogen peroxide is a reaction product which is formed during the enzymatically catalyzed oxidation of substrates such as, for example, glucose, cholesterol, uric acid, glycerol, glycerol phosphate, galactose, pyruvate or sarcosine or by a corresponding oxidase, such as glucose oxidase, cholesterol oxidase, uricase, glycerol oxidase, glycerol phosphate oxidase, galactose oxidase, pyruvate oxidase or sarcosine oxidase. The substrates mentioned belong to the group of analytical substances which play a role in clinical chemistry analysis. The detection of the hydrogen peroxide formed during the oxidase reaction can be by polarography, titrimetry or potentiometry. The colorimetric determination of hydrogen peroxide has increased considerably in importance by the discovery of enzymes which convert hydrogen peroxide, such as peroxidase, catalase or hemoglobin.

Peroxidases, like peroxidatively active substances (for example hemoglobin and methemoglobin) catalyze hydrogen peroxide-dependent oxidation of indicators such a guaiacol, dianisidine hydrochloride or ABTS to give colored compounds. One of the best known detection reactions for hydrogen peroxide is the so-called "Trinder reaction" (Trinder, p. *Ann. Clin. Biochem.*, Vol. 6 [1969], pp. 24–27). 4-Aminoantipyrine is oxidized by hydrogen peroxide in the presence of a peroxidase. The oxidation product is capable of coupling with a phenol or phenol derivative, a quinone-imine dye-stuff and it is possible to determine its concentration by photometry.

The present invention relates to compounds of the general formula I

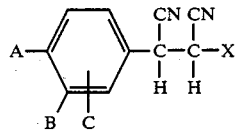

wherein
A is $-NR_2$ or $-OR$,
wherein
R denotes alkyl of 1 to 20 carbon atoms, which can be substituted by halogen or hydroxyl, or
A is $-NH-SO_2-R^1$ or $-NH-CO-R^1$,
wherein
$R^1$ denotes aryl or alkyl of 1 to 20 carbon atoms, or
A is morpholine, piperidine, pyrrolidine or piperazine and
B and C, independently of one another, are hydrogen, alkyl of 1 to 20 carbon atoms, halogen, $-COOH$, $SO_3H$, $-NR_2$, $-OR$, $-NH-SO_2R^1$ or $-NH-CO-R^1$, or A and B together are $-O(CH_2)-O-$ or $-O-CH_2-CH_2-O-$ and
X is CN or $COOR^2$, wherein
$R^2$ is alkyl with up to 3 carbon atoms.

A compound which falls under this definition is 4-(1,2-tricyanoethyl)-N,N-dimethylaniline. This compound was described by McKusiek, B. C. et al in *J. Am. Chem. Soc.*, 80, 2806 (1958), and in particular as an intermediate product in a continuing synthesis, without an indication of other use or application.

Preferred compounds in the context of the invention are those in which aryl represents a phenyl radical which can be substituted by hydroxyl, halogen, $C_1$–$C_3$-alkyl or nitro. Preferred alkyl radicals are those with up to 4 carbon atoms. Halogen is preferably chloring, $R^1$ is preferably phenyl and R is preferably methyl or ethyl. The compounds according to the invention and also 4-(1,2-tricyanoethyl)-N,N-dimethylaniline are especially suitable for use as redox indicators. These compounds are particularly suitable as indicators for qualitative or quantitative detection of hydrogen peroxide or for detection of peroxidases or peroxidatively active substances.

The oxidation of the indicators by hydrogen peroxide or another peroxide (for example, cumene hydroperoxide, strontium peroxide, 2,5-dimethylhexane-2,5-dihydroperoxide, diisopropylbenzoyl hydroperoxide and the like) can be effected by the catalytic action of a peroxidase or a peroxidatively active substance. Suitable peroxidases are those from horseradish or potatoes or those of microbiological origin. Peroxidatively active substances are understood as those substances which catalyze the transfer of the redox equivalents from the hydrogen peroxide or another peroxide to the indicators, such as, for example, hemoglobin, methemoglobin or myoglobin. The compounds of the general formula (I) are furthermore suitable for detecting oxidizing agents such as, for example, persulphate, peracetate, chloramine T or cyanoferri-complexes, such as potassium hexacyanoferrate.

The compounds of the general formula (I) are particularly suitable for use in test agents for substrates such as, for example, glucose, cholesterol, uric acid, glycerol, glycerol phosphate, galactose, pyruvate or sarcosine, which are oxidized by a corresponding oxidase such as glucose oxidase, cholesterol oxidase, uricase, glycerol oxidase, glycerol phosphate oxidase, galactose oxidase, pyruvate oxidase or sarcosine oxidase, in the presence of oxygen to form hydrogen peroxide. The hydrogen peroxide formed is detected using the compounds of the general formula (I).

As has already been mentioned, the compounds of the general formula (I) are also suitable for the detection of peroxidases or peroxidatively active substances. Test systems which may be mentioned here are the detection of occult blood or peroxidase-labeled immune tests.

Test agents or test systems in the context of the present invention are to be understood, for example, as those which can be measured in a cell. In addition to the redox indicators of the general formula (I), the test agents contain all the reagents, such as enzymes, substrates, coenzymes, effectors, antigens, antibodies and the like, necessary for the particular detection of the parameter. These test agents can also contain substances which do not react, such as, for example, buffers, wetting agents and stabilizers. Reagent combinations which are mixed as a powder or solution or are present as tablets or a lyophilisate can be prepared from the reagents and substances mentioned. The reagent combination (if it is not already present as a solution) is taken up in water or another suitable solvent and prepared to give a reagent solution. If the reagent combination consists of individual components, these are to be mixed with one another. After the sample (for example substrate solution, enzyme solution, blood, serum, plasma or urine) has been mixed with an aliquot portion of the reagent mixture, the color formed is measured on a photometer and the particular concentration or substrate concentration is calculated via the molar extinction coefficient and the volumes of reagent and sample added. Both kinetic and end point measurements are possible.

The compounds of the general formula (I) can also be impregnated, together with peroxidase or a peroxidatively active substance, the reagents necessary for the particular detection of the parameter or other enzymes, the buffer system, and if appropriate wetting agents and activators and other auxiliaries, onto absorbent reagent carriers, such as papers, nonwovens and the like. For this, one or more impregnating solutions can be prepared in the form of aqueous or organic or mixed solutions, depending on the dissolving properties of the reagents or auxiliaries. Absorbent carriers or carriers which can swell, preferably filter-paper or absorbent nonwovens of glass or plastic, are impregnated or sprayed with these solutions. The carriers are then dried. The reagent carriers thus prepared can be used either as rapid diagnostics for direct determination of the contents of liquids (for example in body fluids, such as blood, urine or saliva, or in foodstuffs, for example fruit juices, milk or the like). The liquid is applied here directly to the reagent carrier, or the carrier is immersed briefly in the liquid. Semi-quantitative determination is possible by matching the resulting color with a comparison color. Quantitative evaluation can be carried out by reflectance photometry. It is advantageous here that from the compounds of the formula (I) usually develop the dyestuffs which have their absorption maximum in the long-wave range of the spectrum. Light-emitting diodes can then be used as the light source for measurement of such dyestuffs.

When the compounds according to the invention are used in such reagent carriers, also called test strips, it may be advantageous to render the compounds diffusion-resistant. Leaching or "bleeding" of the compounds from the matrix is thereby prevented.

The improvement in diffusion resistance is achieved, for example, by one or more of the substituents R, R¹, R², B or C representing a longerchain alkyl radical. Alkyl radicals of 5 to 20 carbon atoms are preferred for this purpose. Those with 5 to 12 carbon atoms are particularly preferred. These alkyl radicals reduce the solubility of the compounds in aqueous systems.

Another possibility of improving the diffusion resistance is substitution, preferably in the alkyl radicals, in the compounds according to the invention by groups which can interact with other groups, for example from the matrix material.

Those groups or interactions such as are known from the field of ion exchangers are meant here.

It is also possible to introduce the compounds of the general formula (I) into carrier matrices which have been prepared from casting solutions. Examples which may be mentioned here are cellulose, cellulose derivatives, gelatin, gelatin derivatives and plastics, such as polyurethanes and acrylamide. It is advantageous here if the compounds of the general formula (I), and if appropriate the other reagents needed, are added directly to the casting solution, which means that it is possible to prepare the test device consisting of carrier and reagents in one operation.

A reagent solution with which substrates or enzymes can be determined in the cell on the photometer, as described above, can be prepared by eluting the above-mentioned reagents from the absorbent carrier with water or buffer or serum.

Suitable buffers for the test agents mentioned are phosphate, citrate, borate, or buffers with alkali metal or ammonium countrrions. However, other systems can also be used. The pH values sought are 6 to 10, in particular 6.5 to 7.5.

Wetting agents are, in particular, anionic and cationic wetting agents. However, nonionic wetting agents which activate the enzymes can also be used. Sodium lauryl sulphate, dioctyl sodium sulphosuccinate and alkylaryl polyether alcohols are preferred.

Effectors which can be employed are those known for the particular enzymatic reaction.

Other auxiliaries which may be appropriate are customary thickeners, solubilizing agents, emulsifiers, optical brighteners, contrast agents and the like, such as are known in corresponding tests with other chromogens.

The compounds are prepared as follows: a benzylidene compound is dissolved or suspended in an alcohol. Methyl or ethyl alcohol is preferably used here. An alkali metal cyanide, such as, for example, sodium cyanide or potassium cyanide, is then added to this solution or suspension. To achieve a complete reaction, the amount of alkali metal cyanide should be at least equimolar in relation to the amount of benzylidene compound. The alkali metal cyanide is advantageously added in the form of a highly concentrated or saturated aqueous solution. The reaction is an exothermic reaction which proceeds at room temperature. Because of the exothermic reaction, cooling may be necessary. When the reaction has ended, an excess of water is added to the reaction mixture. The excess is usually 4 to 5 times the amount of reaction mixture. After neutralization, the product separates out in crystalline form.

The present invention is described and illustrated in more detail by the examples which follow.

EXAMPLE 1

4-(1,2-Tricyanoethyl)-N,N-dimethylaniline

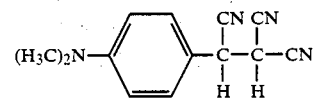

A solution of 7 g (grams) (0.15 mol) of sodium cyanide in 15 ml (milliliters) of water is added dropwise to a solution of 19.7 g (0.1 mol) of 4-dimethylaminobenzylidene-malonic acid dinitrile in a mixture of 100 ml of ethanol and 100 ml of dimethylformamide at room temperature. After 5 hours, 500 ml of water are addd and the clear solution is neutralized with acetic acid. The precipitate which separates out is filtered off with suction and, after drying, 20.4 g (91% of theory) of 4-(1,2-tricyano- ethyl)-N,N-dimethylaniline of melting point 133 to 6° C is obtained.

The following compounds are prepared analogously:

| Example | Structure | Melting Point |
|---|---|---|
| 2 | 3,4-methylenedioxyphenyl-CH(CN)-CH(CN)-CN | 137–139° C. |
| 3 | H₃C—CO—NH—C₆H₄—CH(CN)-CH(CN)-CN | 150–152° C. |
| 4 | (H₃C)₂N—C₆H₄—CH(CN)-CH(CN)-CO₂CH₃ | 116–118° C. |
| 5 | (HO—CH₂—CH₂)₂N—C₆H₃(CH₃)—CH(CN)-CH(CN)-CN | 150–152° C. |
| 6 | H₃CO—C₆H₄—CH(CN)-CH(CN)-CN | 108–110° C. |
| 7 | 3,4-(H₃CO)₂—C₆H₃—CH(CN)-CH(CN)-CN | 138–143° C. |
| 8 | 3,4-(H₃CO)₂—C₆H₃—CH(CN)-CH(CN)-CO₂CH₃ | 76–78° C. |
| 9 | C₆H₅—SO₂—NH—C₆H₃(Cl)—CH(CN)-CH(CN)-CN | 78–80° C. |

Testing of the Compound from Example 1 in a Test System

To detect peroxide in the test system described, the following reagent constituents are taken in a cell.

| | Concentration in the test |
|---|---|
| 1,940 μl of 0.1 M/l citrate buffer, pH = 5, or 0.1 M/l tris buffer, pH = 7 | 97 mmol/l |
| 20 μl of 4-(1,2-tricyanoethyl)-N,N—dimethylaniline | 0.2 mmol/l |
| 20 μl of peroxidase | 9.6 Kμ/l |

Insoluble indicators were prepared as a concentrated stock solution in dimethylformaide or CH₃OH. After measurement of the reagent blank values, the reaction was started by addition of 20 μl (micro liters) of peroxide (0.1 to 10 mmol/l). The extinction maximum measured is at 528 nm (nanometers). Kinetic investigations showed a stable end point after a reaction time of only one minute.

To test the functional capacity and linearity, peroxide concentrations in the range from 0.1 to 1.0 mmol/l were used in the test set-up. The extinction differences measured at 528 nm are summarized in Table 1.

TABLE 1

| $H_2O_2$ (mmol/l) | $\Delta E_{528}$ nm |
|---|---|
| 0.1 | 0.051 |
| 0.2 | 0.111 |
| 0.3 | 0.189 |
| 0.4 | 0.243 |
| 0.5 | 0.307 |
| 0.6 | 0.376 |
| 0.7 | 0.396 |
| 0.8 | 0.478 |
| 0.9 | 0.513 |

TABLE 1-continued

| $H_2O_2$ (mmol/l) | $\Delta E_{528}$ nm |
|---|---|
| 1.0 | 0.581 |

The colorings and extinction maxim obtained with the various indicators are shown in Table 2.

TABLE 2

| Formula | Color | $\lambda$max (nm) |
|---|---|---|
| (structure) | yellow | 432 |
| (structure) | yellow | 402 |
| (structure) | red | 526 |
| (structure) | violet | 546 |
| (structure) | yellow | 400 |
| (structure) | yellow | 428 |

TABLE 2-continued

| Formula | Color | $\lambda$max (nm) |
|---|---|---|
| (structure) | yellow | 416 |

Although the invention has been described with a certain degree of particularity, it is understood that the present disclosure has been made only by way of example and that numerous changes in the details may be resorted to without departing from the scope of the invention.

What is claimed is:

1. A compound selected from the group consisting of

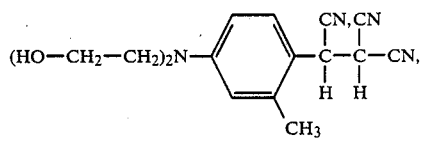

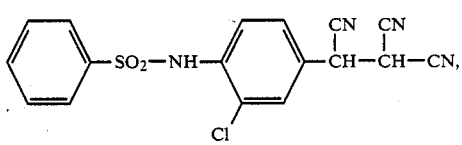

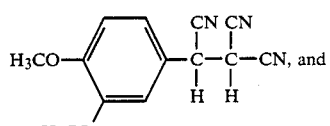, and

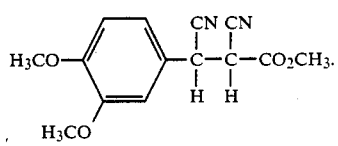

2. A composition for the detection of redox reactions comprising an effective amount of a compound of claim 1.

* * * * *